(12) United States Patent
Daddona, III et al.

(10) Patent No.: US 11,118,144 B2
(45) Date of Patent: Sep. 14, 2021

(54) ANTIMICROBIAL SURFACE CLEANSERS AND BIOSTATIC COATINGS FOR REMOVABLE DENTAL PROSTHETIC APPLIANCES AND ORAL DEVICES

(71) Applicant: CLEARSTREAM TECHNOLOGIES LLC, Charlotte, NC (US)

(72) Inventors: Anthony L Daddona, III, Charlotte, NC (US); James Praechtl, Salsibury, NC (US); Daniel Spagnoli, Southport, NC (US); William Spilfogel, Wellington, FL (US); Simpson E. Adams, III, Mount Pleasant, SC (US); Rebecca L Lister, Tega Cay, SC (US)

(73) Assignee: CLEARSTREAM TECHNOLOGIES, LLC, Charlotte, NC (US)

( * ) Notice: Subject to any disclaimer, the term of this patent is extended or adjusted under 35 U.S.C. 154(b) by 0 days.

(21) Appl. No.: 16/424,977

(22) Filed: May 29, 2019

(65) Prior Publication Data

US 2019/0367843 A1    Dec. 5, 2019

Related U.S. Application Data

(60) Provisional application No. 62/677,327, filed on May 29, 2018.

(51) Int. Cl.
| | | |
|---|---|---|
| *C11D 3/48* | (2006.01) | |
| *C11D 11/00* | (2006.01) | |
| *A61L 2/18* | (2006.01) | |
| *A61L 2/232* | (2006.01) | |
| *B08B 3/08* | (2006.01) | |
| *A01N 55/00* | (2006.01) | |

(52) U.S. Cl.
CPC ............... *C11D 3/48* (2013.01); *A01N 55/00* (2013.01); *A61L 2/18* (2013.01); *A61L 2/232* (2013.01); *B08B 3/08* (2013.01); *C11D 11/0023* (2013.01); *A61L 2202/17* (2013.01); *A61L 2202/21* (2013.01)

(58) Field of Classification Search
None
See application file for complete search history.

(56) References Cited

U.S. PATENT DOCUMENTS

| | | | | |
|---|---|---|---|---|
| 8,956,665 | B2* | 2/2015 | Bolkan | A01N 55/00 424/717 |
| 2007/0065475 | A1* | 3/2007 | Elfersy | A01N 33/12 424/405 |
| 2009/0069270 | A1* | 3/2009 | McMahon | C07F 7/20 514/63 |
| 2016/0058012 | A1* | 3/2016 | Herdt | C09D 5/14 424/407 |

\* cited by examiner

*Primary Examiner* — Danah Al-Awadi
(74) *Attorney, Agent, or Firm* — J. Bennett Mullinax, LLC

(57) ABSTRACT

The invention provides formulations and a process for disinfection, cleansing, and establishing a residual biostatic surface protection for dentures and removable oral appliances. These appliances include complete and partial dentures, removable dental applications, and other products used in an individual's mouth.

4 Claims, 2 Drawing Sheets

ANTIMICROBIAL SURFACE CLEANSERS AND BIOSTATIC COATINGS FOR REMOVABLE DENTAL PROSTHETIC APPLIANCES AND ORAL DEVICES

CROSS REFERENCE TO RELATED APPLICATIONS

This application claims the benefit of U.S. Provisional Application Ser. No. 62/677,327 filed May 29, 2018 and which is incorporated herein by reference.

FIELD OF THE INVENTION

This invention relates to compositions for the care and maintenance of good oral hygiene for users of full or partial dentures or other removable or permanent dental work such as bridges. The invention also relates to methods of making and using such compositions.

The present invention also relates to cleansing formulas that provide disinfection, cleansing, and a residual biostatic protection for dentures and removable oral appliances. These items include complete and partial dentures, removable dental applications, oral care products including splints, retainers, whitening trays, orthodontic aligners, mouth guards, mandibular positioning sleep devices as well as reusable oral products such as hard plastic or metal straws, hydration pack mouth pieces, VAP devices, toothbrushes, anti-snoring devices and infant/child products including bottle nipples, pacifiers, teething rings, and similar devices.

BACKGROUND OF THE INVENTION

It has long been recognized that the formation of dental plaque on teeth can lead to periodontal disease and tooth decay. What is often less recognized is that formation of plaque on full or partial dentures can also cause periodontal disease in gums. People with partial dentures or bridgework may experience tooth decay in remaining natural teeth as a result of plaque on the dental work.

Dental plaque results from cariogenic bacteria (e.g., *Streptococcus mutans*) that collect in colonies and form metabolic acids and deposits on tooth and denture surfaces. Plaque initiates when cariogenic bacteria adhere to the surface of dentures and teeth in the mouth. The metabolic acids produced by the bacteria degrade gum tissue and dental structure. Plaque deposition can lead to tartar buildup and other unsightly and unhealthful consequences.

Many approaches have been tried to prevent or treat plaque and associated calculus (tartar) on teeth, and some approaches have also been tried with dentures including a number of approaches as set forth in the publication Dental Caries: The Disease and its Clinical Management, $2^{nd}$ Ed, 2008 Blackwell Publishing Company and which is incorporated herein by reference for all purposes.

The most straightforward technique for reducing plaque is cleaning or brushing. With teeth, the most common forms of cleaning include brushing with a dentifrice and inundating the oral cavity with a mouth wash or mouth rinse. Dentures may also be brushed or soaked for some period outside the mouth for cleaning and removal of plaque. Depending on the method of attachment in the mouth, partial dental work may or may not be removed for cleaning. Partial dentures and bridgework, therefore, may either be brushed with natural teeth or cleaned separately, like dentures.

For dentures, mechanical cleaning does not always reach all potential areas of plaque attachment. Spaces between teeth or dentures are not always cleaned with the necessary thoroughness. Mouth washes and mouth rinses are often not used for a fully sufficient time to accomplish the necessary cleaning. Denture cleansers are more effective at removing plaque than mouth rinses because they can be used for a longer period of time. Denture cleansers may also contain stronger cleaning ingredients, because the dentures are removed from the mouth before cleaning.

The difficulty inherent with all cleaning approaches is that the bacteria begin to regenerate and form plaque again as soon as cleaning has ended. Thus, cleaning only removes plaque once it has been deposited but can do nothing to prevent plaque from depositing in the first place. Even the strongest cleaning techniques necessarily leave the teeth and dentures exposed to plaque bacteria between cleanings.

Chlorhexidine gluconate and similar materials such as hexetidine are known to adhere to oral tissues and inhibit plaque formation. These compounds may also adhere to acrylic materials. But these compounds have poor organoleptic qualities and can produce significant staining on teeth.

Others have tried to coat dentures using various materials to prevent plaque formation. None of these materials, however, has proven fully effective for dentures. In the case of dentures, the easiest "coating" technique, of course, would be constructing the dentures out of materials that are resistant to plaque attachment. Other techniques have also been tried.

U.S. Pat. No. 415,048 to Lee et al. discloses a liquid paint-on tooth restorative composition. The material comprises barium borosilicate glass and a curable liquid acrylate which hardens on the tooth surface.

U.S. Pat. No. 5,266,305 to Wood et al. discloses the use of copolymers of polyamino acids for the prevention of tartar deposit formation on natural teeth and dentures. The copolymers are formed by the reaction of polysuccinimide with alkyl, alkenyl or aromatic amines and/or alkyl and alkenyl polyamines. The copolymers are incorporated into a toothpaste, gel or mouthwash carrier.

U.S. Pat. No. 5,296,513 to Ige et al. discloses compositions and methods for the preparation of dental polymer shaped articles such as dentures that are resistant to plaque formation. The composition comprises a monomer with at least one (meth)acryloyloxy group, a polyfunctional monomer with two or more (meth)acryloyloxy groups and a monofunctional monomer.

U.S. Pat. No. 5,427,770 to Viccaro et al. teaches toothpaste, gel and mouth wash compositions that include aminoalkyl silicones. Upon use, the silicones bond to the tooth to form a hydrophobic film.

U.S. Statutory Invention Registration No. H83 discloses a number of dental anti-plaque agents comprising certain [ureylenebis (phenylene sulfonylimino)] bis [hydroxynaphthalene sulfonic acids] and derivatives. These compounds inhibit connective tissue destruction and deposition of dental plaque and tartar.

U.S. Pat. No. 8,075,905, incorporated herein by reference and for all purposes, discloses dental materials that may be manufactured from materials and a process that incorporates at least one dispersely distributed cationic surfactant, octenidine salt or a quaternary ammonium cation, dequalinium salt to create an antimicrobial surface on the material used to construct a denture.

The emphasis of previous applications has been directed to incorporating the organosilane quaternary ammonium compounds (SiQAC) into restorative materials. Although this approach has merit, it also has drawbacks such as the need to recertify every material to assure that the SiQAC addition did not modify or compromise the integrity of the material properties. In addition, this approach is only available to new restorations including dentures which, along with other removable or reusable oral appliances and devices, are the target surfaces for extraoral treatment(s) of the invention.

One of ordinary skill in the art recognizes the role that antimicrobials at low concentrations perform as bacteriostatic, fungistatic, algistatic, and viristatic agents. Further, the use of quaternized ammonium compounds (QAC's) have been shown to provide antimicrobial activity when integrated into dental materials such as the commonly known Polymethylmethacrylate (PMMA) which is the primary material in the manufacture of dentures and a focus subject of the invention. As demonstrated in; Antibacterial Quaternary Ammonium Compounds in Dental Materials: A Systematic Review (Mar. 23, 2018) by: Pooyan Makvandia,b, et al. and again in Synthesis and Evaluation of a Novel Antibacterial Dental Resin Composite with Quaternary Ammonium Salts (Mar. 1, 2011) by: Yiming Weng1, et al. Weng teaches that antimicrobial activity is increased by the chain length, but antimicrobial activity decreases upon lengthening the chain beyond C16 within the polymer resin. In addition, Weng shows that compressive strength and composite integrity are compromised as antimicrobial activity is increased by lengthening of the carbon chain.

Quaternary ammonium organosilanes (SiQAC) are often applied from solvent solutions such as lower alcohols and the commercial versions of these quaternized organosilanes are commonly provided as methanolic solutions. Quaternary ammonium functional organosilanes containing hydrolyzable groups such as those sold under the trademark DOW CORNING® 5772 (3-(trimethoxysilyl) propyldimethyloctadecyl ammonium chloride) by Dow Corning Corporation of Midland, Mich. and REQUAT® 1977 (3-(trimethoxysilyl)propylmethyldi(decyl) ammonium chloride) by Sanitized, Inc. of New Preston, Conn. have found a large number of uses because of their ability to attach themselves to a wide variety of substrates where the quaternary ammonium functional group then acts as an antimicrobial and algicidal agent. Substrates treated with such quaternized organosilanes have also been noted to, among other things, be easier to clean, and possess soil release properties.

The references discussed above all look to coating dentures and focus on the base material used in the manufacture of the denture. Like teeth, however, dentures are subject to wear, and a plaque-resistant material may not continue to be resistant over time. Moreover, the plaque-resistant materials available for denture construction are not always the best materials for other design objectives. What remains missing in the art is an acceptable coating material that can be used with full or partial dentures or dental work to provide a plaque resistant coating for dentures and permanent dental work. Such a coating should be able to be reapplied regularly, during normal cleaning, and should offer superior resistance to plaque formation. Accordingly, there remains room for variation and improvement within the art.

SUMMARY OF THE INVENTION

It is one aspect of at least one of the present embodiments of the invention to provide for a composition for preventing microbial growth on dental surfaces in which the composition comprises an effective amount of:
at least one quaternary ammonium compound as a disinfectant; a non-ionic surfactant; and, a chelating agent. In one embodiment, the composition's at least one quaternary ammonium compound is a blend of at least two different chain lengths and which are present at a concentration of between about 0.2 to about 20 weight %, the non-ionic surfactant is present at a concentration between about 0.003 to about 0.5 weight %, and the chelating agent is present at a concentration of between about 0.01 to about 10 weight %.

The composition may further comprise a quaternary ammonium organosilane present in a concentration of between about 0.01 to about 5.0 weight % and which provides an anti-microbial coating to the surfaces of a treated oral appliance. Further, the composition incorporating the quaternary ammonium compound is a blend of substantially equal parts of alkyl dimethyl benzyl ammonium chloride having a chain length of C 12-18 and alkyl ethyl benzyl ammonium chloride having a chain length of C12-14.

In at least one embodiment of the invention the aqueous composition for cleaning dentures contains therein an anti-microbial coating solution, the anti-bacterial coating consisting of a quaternary ammonium organosilane. The quaternary ammonium organosilane may be present in an amount of about 0.01 to about 5.0 weight % and may further utilize, the quaternary ammonium organosilane of 3-(trimethoxysilyl) propyloctadecyldimethyl ammonium chloride.

At least one embodiment of the present invention is directed to an oral appliance containing an anti-microbial coating on the exterior surface of the device, the coating comprising a quaternary ammonium organosilane according to the formula of:

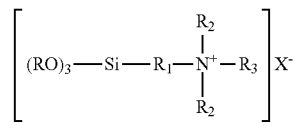

Wherein:
R is an alkyl group, preferably $C_1$-$C_4$;
$R_1$ is an alkyl group, preferably $C_1$-$C_8$;
$R_2$ is and alkyl group, preferably $C_1$-$C_8$;
$R_3$ is an alkyl group, preferably $C_{11}$-$C_{22}$; and
X is the counter ion, a halide, preferably $Cl^-$ or $Br^-$.

The oral appliance is treated by the step of exposing a surface of the oral appliance to a cleaning composition as described above and may include the step of providing an anti-microbial coating to a surface of an oral appliance comprising the step of applying a coating composition as detailed above.

A further treatment process of an oral appliance includes the steps of surface treatment of an oral appliance comprising the steps of:
exposing a surface of the oral appliance to a cleaning composition set forth herein and subsequently exposing the surface of the oral appliance to an anti-microbial coating solution additionally set forth herein, the treated oral appliance having a sanitized surface, the sanitized surface additionally having an anti-microbial coating comprising a quaternary ammonium organosilane.

Another aspect of the invention is to provide specific products and process using the products that not only cleanse dentures and other removable and reusable oral devices but may also be used to modify the surfaces of these devices and make them less susceptible to the formation of mature plaque.

It is one aspect of at least one of the present embodiments to provide for an aqueous composition preventing microbial growth on dentures and removable oral devices in which the composition contains an effective amount of:
- ethoxylated fatty alcohol (non-ionic surfactant);
- quaternary ammonium chloride compounds;
- chelating agent; quaternary ammonium organosilane (SiQAC).

In another aspect of at least one of the present embodiments to provide for a composition for preventing microbial growth on dentures and removable oral devices in which the composition comprises a residual antimicrobial component that remains bound to the cleaned and disinfected dental surface thereby inhibiting and reducing microbial growth and biofilm formation.

These and other features, aspects, and advantages of the present invention will become better understood with reference to the following description, figures, and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Figure 1:
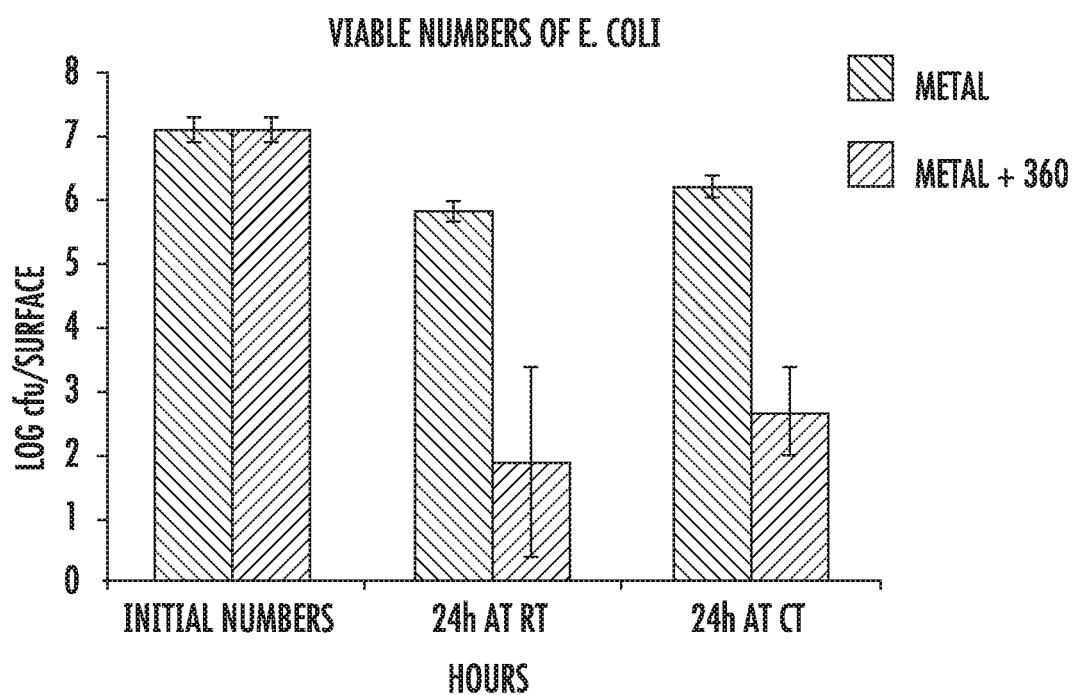
FIG. 1 is a graph setting forth data for SiQAC coated (metal+360) stainless-steel coupons which demonstrate a 5.8-log reduction of Listeria innocua after a 24 hour incubation period at room temperature and cold temperature versus the control (metal).

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

As used herein, the term "effective amount" means the stated value or range, plus or minus 10%, unless a more specific value or range is provided. Formulations which may be listed or claimed as "comprising of" may also be used as formulations listed or claimed as "consisting of."

In describing the various figures herein, the same reference numbers are used throughout to describe the same material, apparatus, testing procedures, or process pathway. To avoid redundancy, detailed descriptions of much of the apparatus or processes, once described in relation to a figure or an embodiment is not repeated in the descriptions of subsequent figures or embodiments, although such apparatus or process may be labeled with the same reference numbers.

The present invention relates to a sodium hypochlorite and sodium lauryl sulfate free antimicrobial and cleansing formulas that provides disinfection, cleansing, and residual biostatic protection for dentures and removable oral appliances. The invention also relates to the composition's formulae in concentrated, diluted, ready to use (RTU), and includes post manufactured-preinstalled treatments of dentures and other oral devices including those referenced herein.

The formulas of this invention comprises a chemical composition which includes a combination of quaternary ammonium compounds (QAC) buffers, detergent agents, chelating agents, ethoxylated fatty alcohols, and silicone quaternary ammonium salts (SiQAC) which provide an effective amalgamation of cleansing, disinfection, and residual anti-microbial surface protection for dentures, removable orthodontic braces, bridges, and other removable or temporary oral devices and appliances such as; TMJ splints, anti-snoring devices, athletic mouth guards and oral infant devices. These and other features, aspects, and advantages of the present invention will become better understood with reference to the following description and appended claims.

The various formulas provided herein includes cleansing agents, chelating agents to remove scale, surfactants to render the polymer surface less susceptible to pellicle formation, and a dual-purpose silane coating. Silane has high covalent bonding affinities to polymers and it also becomes incorporated into surface imperfections such as micro scratches. Silane renders surfaces more abrasion resistant, and by reducing defect edges renders the surface less susceptible to microbial attachment and the onset of plaque.

Silane may also bound to n-alkyl (C12, C14, C16, C18, C20, C22) dimethyl benzyl ammonium chloride to form Silane Quaternary Ammonium Compounds (SiQAC) which imparts residual antimicrobial properties to the surface. A combination of the above components renders a dean prosthesis with a surface that is less susceptible to microbial attachment.

The formulas help remove and prevent the formation of dental plaque and tartar, thereby retarding the accumulation of biofilms and plaque on the surfaces of prosthetic, removable, or temporary oral appliances and devices. This may further aid in the reduction of other ailments such as heart disease, other systemic conditions, ulcerative lesions, or painful infective inflammation caused by trapped microorganisms such as *Candida albicans* that are traced back to poor hygienic oral care.

The cleaning compositions and the protective, anti-microbial, film forming coating compositions are described below and are further provided in Tables 1-4.

TABLE 1

| Concentrate Cleanser | Wt. % |
|---|---|
| Water | 49.38 |
| Citric Acid | 12.50 |
| Potassium Hydroxide 45% | 22.70 |
| Rolfor 25/9 | 0.17 |
| Maquat MQ 2525 80% | 0.25 |
| Uniquat QAC 50 | 10.00 |
| Versene 100 | 5.00 |
| | 100.00 |

TABLE 2

| Concentrate Cleanser w/SiQAC | Wt. % |
|---|---|
| Water | 48.38 |
| Citric acid | 12.50 |
| Potassium hydroxide 45% | 22.70 |
| Rolfor 25/9 | 0.17 |
| Maquat MQ 2525 80% | 0.25 |
| Uniquat QAC 50 | 10.00 |
| Ztrex 72 MUP | 1.00 |
| Versene 100 | 5.00 |
| | 100.00 |

TABLE 3

| Ready To Use (RTU) | |
|---|---|
| Cleanser | Wt. % |
| Water | 89.99 |
| Glucamate LT | 3.00 |
| Sodium bicarbonate | 3.00 |
| Citric acid | 2.00 |
| Potassium monopersulfate | 1.00 |
| Sodium carbonate | 0.10 |
| Sodium percarbonate | 0.50 |
| Versene 100 | 0.10 |
| Maquat MQ 2525 80% | 0.25 |
| Sun Pure Turpin | |
| Orange Fragrance (3% concentrate) | 0.06 |
| | 100.00 |

TABLE 4

| Ready To Use (RTU) w/SiQAC | |
|---|---|
| Cleanser w/SiQAC | Wt. % |
| Water | 89.59 |
| Glucamate LT | 3.00 |
| Sodium bicarbonate | 3.00 |
| Citric acid | 2.00 |
| Potassium monopersulfate | 1.00 |
| Sodium carbonate | 0.10 |

TABLE 4-continued

| Ready To Use (RTU) w/SiQAC | |
|---|---|
| Cleanser w/SiQAC | Wt. % |
| Sodium percarbonate | 0.50 |
| Versene 100 | 0.10 |
| Maquat MQ 2525 80% | 0.25 |
| Ztrex 72 MUP | 0.40 |
| Sun Pure Turpin | |
| Orange Fragrance (3% concentrate) | 0.06 |
| | 100.00 |

One preferred cleaning composition may comprise the following: about 0.003 to about 0.5 wt. % of ethoxylated fatty alcohol; about 0.005 to about 0.5 wt. % of a blend to equal parts of alkyl dimethyl benzyl ammonium chloride (C 12-18) and alkyl ethyl benzyl ammonium chloride (C12-14); about 0.2 to about 20 wt. % of n-alkyl (C12, C14, C16) dimethyl benzyl ammonium chloride; about 0.1 to about 10 wt. % of tetrasodium ethylenediaminetetraacetate; and about 0.01 to about 5 wt. % of 3(trimethoxysilyl) propyldimethyloctadecyl ammonium chloride (SiQAC).

Suitable nonionic surfactants that can be added to the composition include the polyoxyethylene-polyoxypropylene condensates, which are sold by BASF under the tradename "Pluronic", polyoxyethylene condensates of alkyl phenols; polyoxyethylene condensates of aliphatic alcohols/ethylene oxide condensates having from 1 to 30 moles of ethylene oxide per mole of coconut alcohol; ethoxylated long chain alcohols sold by Shell Chemical Co. under the tradename "Neodol," or sold by Sasol North American, Inc. under the tradename "Sasol," polyoxyethylene condensates of sorbitan fatty acids, sorbitan dialkylesters, sorbitan alkylesterethylene glycol condensates, aliphatic alcohol polyeth-ylene glycol condensates, alkylphenol polyethylene glycol condensates, polypropylene glycol polyethylene glycol condensates, alkanolamides, such as the monoalkoanolamides, dialkanolamides and the ethoxylated alkanolamides, for example coconut monoethanolamide, lauric isopropanolamide and lauric diethanolamide; and amine oxides for example dodecyldimethylamine oxide.

Suitable nonionic surfactants also include, inter alia, condensation products of alkylene oxide groups with an organic hydrophobic compound, such as an aliphatic compound or with an alkyl aromatic compound. The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy hydrophobic and hydrophilic elements may be varied to adjust these properties.

An example of such a nonionic surfactant is the condensation product of one mole of an alkylphenol having an alkyl group containing from 6 to 12 carbon atoms with from about 5 to 25 moles of an alkylene oxide. Another example of such a nonionic surfactant is the condensation product of one mole of an aliphatic alcohol which may be a primary, secondary or tertiary alcohol having from 6 to 18 carbon atoms with from 1 to about 10 moles of alkylene oxide. Suitable alkylene oxides can be either ethylene oxides or propylene oxides or mixtures thereof. Suitable nonionic surfactants also include primary and secondary linear and branched alcohol ethoxylates, such as those based on C10 to C16 alcohols which further include an average of from 3 to 10 moles of ethoxylation per mol of alcohol Particularly preferred nonionic surfactants are C11 linear primary alcohol ethoxylates averaging about 9 moles of ethylene oxide per mole of alcohol. These surfactants are available, for example, under the commercial name of Neodol 1-9, (from Shell Chemical Company, Houston, Tex.), or in the Genapol® series of linear alcohol ethoxylates, particularly Genapol® 26-L-60 or Genapol® 26-L-80 (from Clariant Corp., Charlotte, N.C.).

A further class of nonionic surfactants which are advantageously present in the inventive compositions are those presently marketed under the Genapol® trade name. Particularly useful are those in the Genapol® "26-L" series which include for example: C12-16 linear alcohols condensed with 1 mole of ethylene oxide (Genapol® 24-L-3); C12-16 linear alcohols condensed with 1.6 moles of ethylene oxide (Genapol.® 26-L-1.6); C12-16 linear alcohols condensed with 2 moles of ethylene oxide (Genapol® 26-L-2); C12-16 linear alcohols condensed with 3 moles of ethylene oxide (Genapol® 26-L-3); C12-16 linear alcohols condensed with 5 moles of ethylene oxide (Genapol® 26-L-5); as well as C12-16 linear alcohols condensed with varying amounts of ethylene oxide to provide specific cloud points of the surfactant (i.e., Genapol® 26-L-60, Genapol® 26-L-60N, and Genapol® 26-L-98. These materials are commercially available from Clariant Corp. (Charlotte, N.C.).

It is to be understood that nonionic surfactants other than those described above may also be used. By way of illustration, and not by way of limitation, examples include secondary C12 to C15 alcohol ethoxylates, including those which have from about 3 to about 10 moles of ethoxylation. Such are available in the Tergitol® series of nonionic surfactants (Union Carbide Corp., Danbury, Conn.), particularly those in the Tergitol® "15-S-" series. Further exemplary nonionic surfactants include linear primary C11 to C15 alcohol ethoxylates, including those which have from about 3 to about 10 moles of ethoxylation. Such are available in the Neodoll® series of nonionic surfactants (Shell Chemical Co.) N-alkyl pyrrolidones such as marketed under the tradename "Surfadone," ISP Investment Corp., Wayne, N.J. are also useful. Flurosurfactants can also be used. Preferably, the fluorinated surfactant for use in the present invention is a fluorinated hydrocarbon. Examples of fluorinated surfactants for use in the present invention include Zonyl FSO Fluor-osurfactant (described as a perfluoroalkyl ethoxylate) available from E.I. DuPont de Nemours & Co., Inc., and Fluorad FC-430 surfactant (described as a fluoroaliphatic polymeric ester) available from the Industrial Chemical Products Division of 3M.

A preferred ethoxylated fatty alcohol is Rolfor 25-9, a non-ionic surfactant available from Lamberti synthesis USA, Inc. in Hungerford, Tex.

The non-ionic surfactant can be present in a range from about 0.003 to about 0.5 wt. % and more preferably present in a concentration of about 0.17 wt. %

Suitable quaternary ammonium compounds that can be added to the composition include the groups as characterized by USEPA.

Group I: The alkyl or hydroxyl (straight chain) substituted Quats;

Group II: The non-halogenated benzyl substituted. Quats (including hydroxybenzyl, hydroxyethylbenzyl, naphylmethyl, dodecyhlbenzhyl, and alkyl benzyl);

Group III: The di- and tri-chlorobenzyl substituted Quats;

Group IV: Quats with unusual substitutes (charged heterocyclic compounds)

One of the preferred quaternary ammonium compounds is Maquat MQ 2525 80%. This compound is a quaternary ammonium compound blend of an alkyl dimethyl benzyl ammonium chloride (C 12-18) in a weight percent of about 40 to 43 percent in combination with an alkyl ethyl benzyl ammonium chloride (C12-14) also present in a weight percent of about 40 to 43 percent and is available from Mason Chemical. Company in Arlington Heights, Ill.

The quaternary ammonium compound can be present in a concentration range of about 0.005 to about 0.5 wt. % and more preferably as a concentrate of about 0.25 wt. %.

Another preferred quaternary ammonium compound is Uniquat QAC 50. This product is a blend of n-alkyl (C12, C14, C16) dimethyl benzyl ammonium chloride in a weight percent of about. 50 percent in a water ethanol mixture and is available from Lanza (Basel, Switzerland). It is present in a range of about 0.2 to about 20 wt. % and preferably at a concentration of about 10 wt. %.

A preferred chelating agent is Versene 100 (EDTA) a chelating agent available from Dow Chemical (Midland, Mich.) and has an active ingredient of tetrasodium ethylenediaminetetraacetate. It may be present in a concentration of about 0.01 to about 10.0 wt. % and is preferably at a concentration of about 5.0 wt. %.

A preferred rheology modifier is Glucamate LT which is an ethoxylated methyl glucose ether which has been esterified with oleic acid and is available from Lubrizol (Wickliffe, Ohio). It is present in a range of about 0.3 to about 10 wt. % and is preferably at a concentration of about 3 wt. %.

The residual anti-microbial properties of the formulation seen in Tables 2 & 4 are the result of the film-forming quaternary ammonium organosilane as shown in the following structural representation:

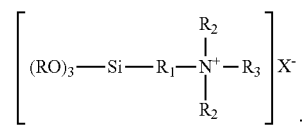

Wherein:
R is an alkyl group, preferably $C_1$-$C_4$;
$R_1$ is an alkyl group, preferably $C_1$-$C_8$;
$R_2$ is and alkyl group, preferably $C_1$-$C_8$;
$R_3$ is an alkyl group, preferably $C_{11}$-$C_{22}$; and
X is the counter ion, a halide, preferably $Cl^-$ or $Br^-$.

Specific non-limiting quaternary ammonium organosilanes within the scope of the invention are represented by the following molecular formulas:

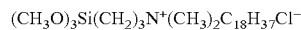

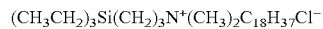

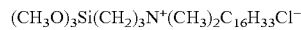

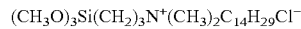

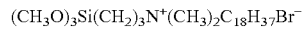

The preferred quaternary ammonium organosilane is Ztrex 72 MUP. This product is a silicone quaternary ammonium salt available from Piedmont Chemical. Industries (High Point, N.C.) having an active ingredient of 3-(trimethoxysilyl) propyldimethyloctadecyl ammonium chloride. The Ztrex 72 MUP may optionally be included in a formulation and may be at a range of about 0.01 to 5 wt. %, more preferably at a concentration of about 1.0 wt. % as set forth in Table 2 and still more preferably for certain embodiments at a concentration of about 0.4 wt. % as set forth in Table 4. The SiQAC compounds such as Ztrex 72 MUP are typically in a methanol solvent. While methanol is a preferred solvent, other lower alcohols, C1 to C4, can be used. Typically, the solvent will be present in amounts of about 10 to 50 percent by weight of the SiQAC.

Additional Additives

As set forth in Tables 1 and 2, additives of citric acid, potassium hydroxide or sodium hydroxide may be present along with the appropriate amount of water.

Citric acid may be present at about 0.25 to 20 wt. % and, more preferably present in a concentration of about 12.5 wt. %.

Potassium hydroxide (45 wt. %) may be present at about 0.45 to 30 wt. % and more preferably present in a concentration of about 22.7 wt. %.

Water may be present at about 30-99 wt. % and more preferably present in a concentration of about 49 wt. % as set forth in Tables 1 and 2 and preferably in a concentration of about 90 wt. % as set for in Tables 3 and 4.

The formulations seen in Tables 1 and 3 (cleaning) and Tables 2 and 4 (cleaning with protective anti-microbial surface treatment) provide for an effective chemical composition that can be used to treat dentures, and removable oral devices which will impart a persistent anti-microbial surface. In so doing, the coated surfaces will resist microbial growth and biofilm formation, therefore significantly lessening the onset of a range of periodontal diseases.

The formulations seen in Table 1 and Table 2 are for a concentrated formulation. A range from about 1:25 to 1:125 can provide for a useful coating composition for application to dentures and removable oral devices. Effective amounts of other various additives may be added in combination with the ingredients as set forth in Tables 1, 2, 3 and 4. These would include:

Rheology modifiers such as but not limited to: methyl glucose ether, xanthan gum or sodium carboxymethylcellulose and preferably ethoxylated methyl glucose ether present at about 0.3 to about 10 wt. % and preferably at about 3 wt. %;

pH modifiers such as but not limited to lime, sodium silicate, sodium phosphates and preferably sodium carbonate added at about 0.0.1 to 1 wt. % and preferably at a concentration of about 0.1 wt. %;

detergent agents such as alkali metal salts which include but not limited to sodium bicarbonate present at about 0.3 to about 6 wt. % and preferably at about 3 wt. %, potassium monopersulfate present at about 0.1 to 5 wt. % and preferably at about 1 wt. %, and sodium percarbonate present at about 0.05 to about 5 wt. % and preferably at about 0.5 wt %.

Other additives may include glycol solvents such as but not limited to:

glycerol and propylene glycol present at about 0 to about 30 wt. %;

fragrances such as but not limited to Sun Pure Turpin for orange fragrance (3% concentrate) present at about 0.01 to about 1 wt. % and preferably at about 0.06 wt. %; and, colorants such as but not limited to FD&C Blue No 1 present at about 0 to about 1 wt. %.

Preferably, the concentrate is mixed with water such that the concentrate is present at a dilution of about 1:50 though a pH range of 4.0 to 6.5. is preferred for good bonding of the protective chemicals to the various surfaces. Buffered compositions from pH 3 to 4 and from pH 6.5 to about 9.5 may also be used.

Preparation of Formula

Raw materials are added in order of addition as listed in the formulas for Table 1 and Table 2. To an empty and clean mixing vessel add the water and start stirring until vortex is formed. While mixing add citric acid and potassium hydroxide and stir for 10 minutes maintaining vortex. Add Rolfor 25-9 mix for 10 minutes maintaining vortex. Add the remaining raw materials and mix for 10 minutes maintaining vortex.

Raw materials are added in order of addition as listed in the formulas for Table 3 and Table 4. Charge mixing vessel with water, begin stirring until a vortex is formed. While mixing add Glucamate LT, sodium bicarbonate, citric acid, potassium monopersulfate, sodium carbonate and sodium percarbonate and stir for 10 minutes maintaining a vortex. Add the remaining raw materials and mix for 10 minutes maintaining vortex.

Testing

The following test procedure was done to mimic the cleansing of dentures.

Polymethylmethacrylate (PMMA), a material typically used for forming dentures was used as the test surface to demonstrate film formation of the SiQAC on the surface of the PMMA coupons as a result of repetitive applications. Another objective was to test for efficacy of the SiQAC coating when exposed to microbes.

The composition from Table 2 was applied to PMMA coupons, 50 mm by 50 mm. The PMMA coupons were disinfected rinsed and dried in preparation for the test. The composition shown in Table 2 (cleanser with SiQAC) was diluted with water to make a 1:50 dilution and the PMMA coupons were placed into the solution to soak for five minutes with gentle agitation.

After five minutes the PMMA coupons were brushed, with a soft denture brush (Oral-B, Ultra Soft) for 30 brush cycles on each side of the coupons. The coupons were then rinsed and placed on a drying rack exposed to a fan.

When the coupons were dried, they were placed into a fresh solution of cleanser with SiQAC and soaked again for five minutes with gentle agitation, brushed for 30 brush cycles on each side, rinsed, and dried exposed to a fan. This cycle was repeated ten times.

At the end of the tenth cycle the coupons were treated with bromophenol blue to test for the presence of the SiQAC bonded to the surface. The coupon surfaces turned blue which indicated the SiQAC was bonded to the surface. The anion of bromophenol blue is complexed with the cation of the SiQAC; the presence of a blue color indicates antimicrobial protection.

Some of the coupons were held out at the first soak and were treated with bromophenol blue. The first soak also turned blue demonstrating the onset of film formation of the SiQAC with only one soak and brushing.

PMMA coupons were tested for antimicrobial efficacy according to test method JIS Z 2801, Test for Antimicrobial Activity of Plastics. The JIS Z 2801 procedure has been adopted as an International Organization for Standardization (ISO) procedure, ISO 22196.

The test microorganism *Candida albicans* was used and was grown in a liquid culture medium. The suspension of the test microorganism was standardized by dilution in a nutritive broth and control and test surfaces were inoculated with microorganisms, in duplicate, and then the microbial inoculum was covered with a thin, sterile film.

Microbial concentrations were determined at "time zero" by elution followed by dilution and plating. A control was run to verify that the neutralization/elution method effectively neutralized the antimicrobial agent in the antimicrobial surface being tested.

Inoculated, covered control and antimicrobial test surfaces were allowed to incubate undisturbed in a humid environment for one hour.

After incubation, microbial concentrations were determined. The reduction of microorganisms relative to initial concentrations and the control surface was calculated.

Results

Control, and antimicrobial test surfaces inoculated with *Candida albicans* were allowed to incubate undisturbed in a humid environment for 24 hours as set forth in Table 5.

The rest of the inoculated samples were stored at 35° C. for 24 hours,

The efficacy of the SiQAC coating was determined using the same enumeration method described above.

Results

Figure 2:
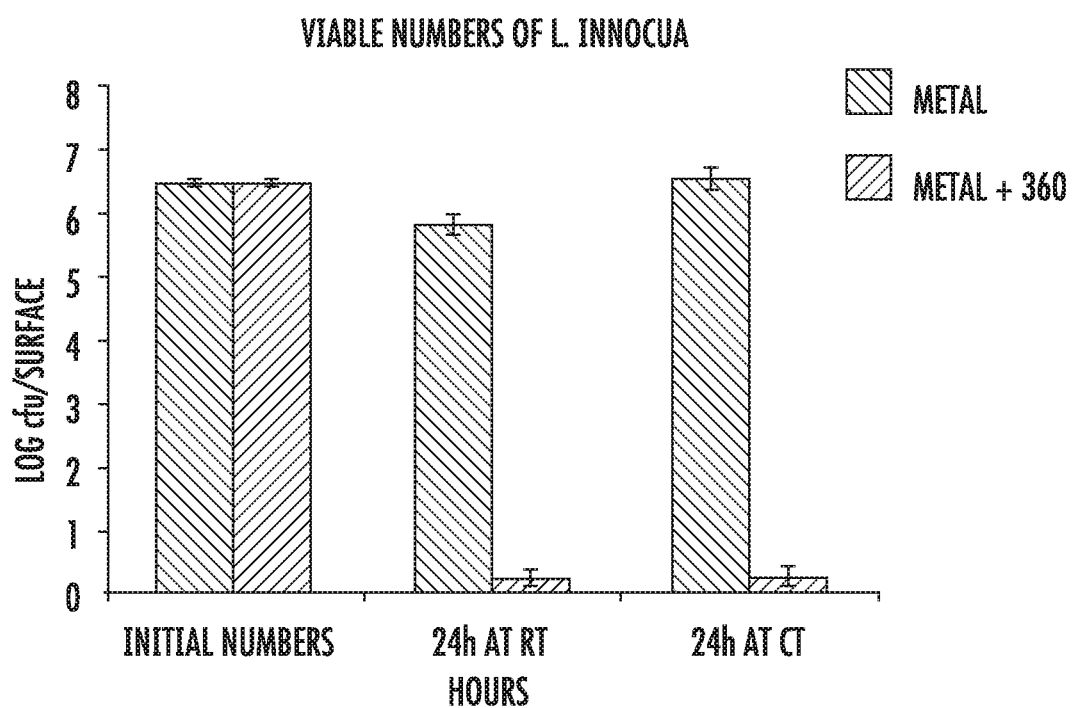
FIG. 2 is a graph setting forth data of SiQAC coated (metal+360) stainless-steel coupons which demonstrate for E. coli a 5-log reduction at a 24 hour incubation period at room temperature and a 4.5-log reduction at cold temperature versus the control (metal).

Results for efficacy testing on two foodborne bacteria (*Listeria innocua* and *Escherichia coli*) are shown in FIGS. 1 and 2. Data was collected using a protocol where a 0.1 ml aliquot of bacterial cell suspension (~$10^6$ colony forming unit/ml) in a 1/500 dilution of nutrient broth was inoculated onto both stainless steel coupon surfaces control (metal) and SiQAC coated (metal+360) which were then covered with a piece of film measuring 20 mm×20 mm and gently press down so that the bacterial inoculum spreads to the edges of the sample. The samples were stored in sealed jars at ~70°

TABLE 5

| Test Microorganism | Contact Time | Test Substance | Replicate | CFU/Carrier | Average CFU/Carrier | Average Percent Reduction Compared to Treated Time Zero | Average $Log_{10}$ Reduction Cmpared to Treated Time Zero |
|---|---|---|---|---|---|---|---|
| *C. albicans* ATCC 10231 | Time Zero | Control | 1 | 7.50E+03 | 6.75E+03 | | N/A |
| | | | 2 | 6.00E+03 | | | |
| | | SIQAC treated | 1 | 3.45E+04 | 3.15E+04 | | N/A |
| | | | 2 | 2.85E+04 | | | |
| | 24 hours | Control | 1 | 1.45E+04 | 1.58E+04 | | N/A |
| | | | 2 | 1.70E+04 | | | |
| | | SiQAC treated | 1 | <5.00E+00* | <5.00E+00 | >99.98 | >3.80 |
| | | | 2 | <5.00E+00* | | | |

*Limit of detection is 5.00E+00, values below this limit are reported as <5.00E+00 in the table.

The SiQAC treated PMMA coupon demonstrated a log reduction of greater than 3.8 as compared to the control which had increased in count.

A further test for antimicrobial efficacy was done on stainless-steel coupons, 50 mm by 50 mm. One objective was to test the ability of the SiQAC coating to minimize the bacterial contamination on the stainless-steel surface over a sustained period of time.

Another objective was to evaluate the growth or survival of the bacterial strains transferred to a SiQAC, coated, metal surface compared with an uncoated metal surface as a control. The bacteria used was *Listeria innocua* as a surrogate for *Listeria monocytogenes* (Rod shaped Gram positive bacterium) and *Escherichia coli* K12 as a surrogate for *Escherichia coli* O157:H7 (Gram negative rods).

The stainless-steel coupons were stored at room temperature (23°).

One set was coated with SiQAC and the other set was not coated (control). Each stainless-steel coupon was placed in separate sterile Petri dishes with the test surface uppermost. A 0.2 ml aliquot of bacterial cell suspension (~$10^6$ colony forming unit/mi) in a nutrient broth was inoculated onto the metal surface and then covered with a piece of sterile film measuring 20 mm×20 mm and gently press down so that the bacterial inoculum spread to the edges of the sample. Each petri dish was then covered.

A 10 ml aliquot of a suitable neutralizing solution was added to half of the prepared samples. This was applied using a pipette to collect and release the nutrient broth at least four times. A stomacher was used to maximize the recovery rate of the bacterial survivors. The survivors were collected and transferred to test-tubes containing diluent water and appropriate neutralizing chemicals.

For the plate counting method, modified tryptic soy agar (MTSA) was used as the growth medium for enumeration of the bacteria survivors.

F. room temperature (RT) and ~52° F. cold temperature (CT) at ~95% RH for 24 h. As used herein, the term "360" refers to the cleanser with SiQAC as described above.

The survivors were collected by cotton swab method and transferred to test-tubes containing diluent water and neutralizing chemicals. For the plate counting method, tryptic soy agar was used as the growth medium for enumeration of the bacteria survivors.

As shown in FIG. 1, SiQAC coated (metal+360) stainless-steel coupons demonstrate a 6-log reduction of *Listeria innocua* after a 24 hour incubation period at room temperature and cold temperature versus the control (metal).

In FIG. 2 the MAC coated (metal+360) stainless-steel coupons demonstrate a 5-log reduction at a 24-hour incubation period at room temperature and a 4.5-log reduction at cold temperature for *E. coli* versus the control (metal).

Figure 3:
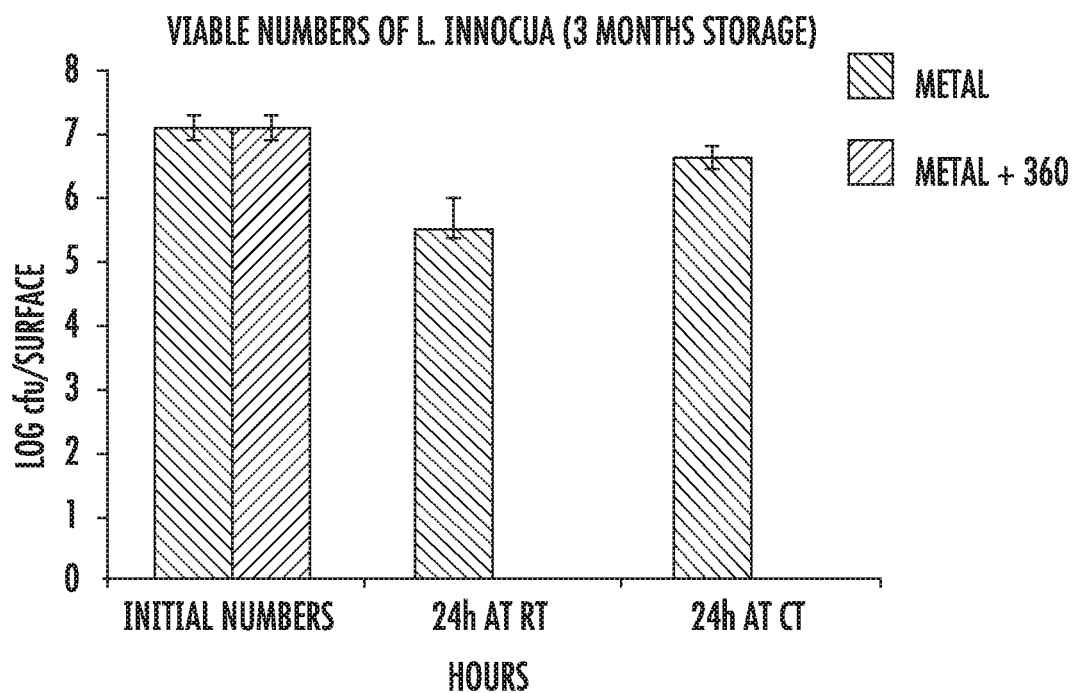
FIG. 3 is a graph setting forth data for 3 month storage of SiQAC coated (metal+360) stainless-steel coupons which demonstrate a 6.5-log reduction of Listeria innocua after a 24 hour incubation period at room temperature and cold temperature versus the control (metal).
Figure 4:
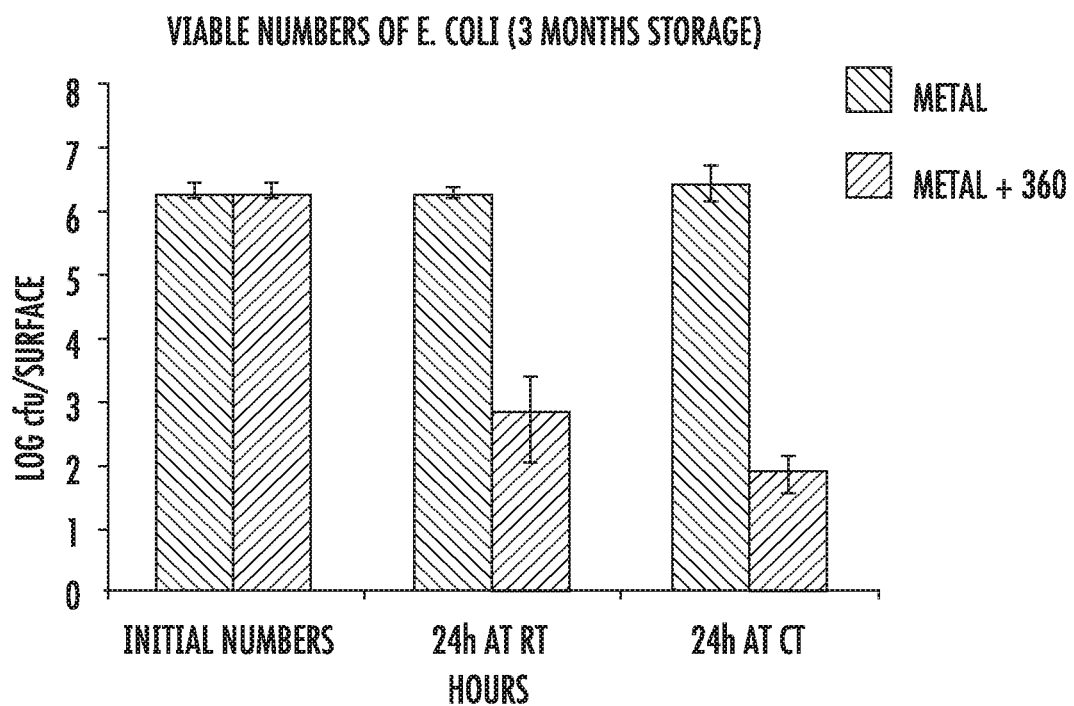
FIG. 4 is a graph setting forth data for 3 month storage of SiQAC coated (metal+360) stainless-steel coupons which demonstrate a 3.5-log reduct of E. coli after a 24 hour incubation period at room temperature and a 4.5-log reduction at cold temperature versus the control (metal).

Results for efficacy testing on two foodborne bacteria (*Listeria innocua* and *Escherichia coli*) after three months of storing the SiQAC coated stainless-steel coupons are shown in FIGS. 3 and 4.

Data was collected using a protocol where 0.1 ml aliquot of bacterial cell suspension (~$10^6$ colony forming unit/ml) in a 1/500 dilution of nutrient broth was inoculated onto both stainless steel surfaces, control coupon (metal) and SiQAC coated coupon (metal+360). Both control and SiQAC coated coupon surfaces were covered with a piece of film measuring 20 mm×20 mm and gently press down so that the bacterial inoculum spreads to the edges of the sample. The samples were stored in sealed jars at ~70° F. (RT) and ~52° F. (CT) at >95% RH for 24 h.

The survivors were collected by cotton swab method and transferred to test-tubes containing diluent water and neutralizing chemicals. For the plate counting method, tryptic soy agar was used as the growth medium for enumeration of the bacteria survivors.

As seen in FIG. 3, there is a 6.5-log reduction or no measurable counts of *Listeria innocua* after three months of storing the SiQAC coated stainless-steel coupons. FIG. 4 demonstrates a 3-log reduction at room temperature and a 4-log reduction at cold temperature for *E. coli* after three months of storing the SiQAC coated stainless-steel coupons.

Another test used for antimicrobial testing was ASTM E2315, completed by a third-party lab. ASTM E2315 is a quantitative test guide designed to assess changes in the population of microorganisms in an antimicrobial liquid suspension. The ASTM E2315 guide is versatile and can be conducted using contact times ranging from ten seconds to 24 hours. The ASTM E2315 test guide uses non-antimicrobial agents as inoculum population controls to establish baselines for microbial reductions.

The composition shown in Table 1 (cleanser) was diluted with water to make a 1:50 dilution. This diluted solution was evaluated according to the ASTM E2315 test method for antimicrobial efficacy. The microorganism used for this test was *Candida albicans* ATCC 10231.

Dilutions of the neutralized test solution are assayed using appropriate growth media to determine the surviving microorganisms at the respective contact times. Reductions of microorganisms are calculated by comparing initial microbial concentrations to final microbial concentrations. Results are set forth in Table 6.

TABLE 6

| Test Microorganism | Test Substance | Contact Time | Replicate | CFU/mL | Average CFU/mL | Average Percent Reduction Compared to Control | Average $Log_{10}$ Reduction Compared to Control |
|---|---|---|---|---|---|---|---|
| *C. albicans* ATCC 10231 | Control (PBS) | Time Zero | 1 | 5.00E+07 | 5.04E+07 | N/A | |
|  |  |  | 2 | 5.75E+07 |  |  |  |
|  | Control (PBS) | 5 minutes | 1 | 4.40E+07 |  |  |  |
|  |  |  | 2 | 5.00E+07 |  |  |  |
|  | Table 1 Composition diluted 1:50 |  | 1 | 5.00E+01 | 1.00E+02 | 99.9998% | 5.7 |
|  |  |  | 2 | 1.50E+02 |  |  |  |

As shown in Table 6, the 1:50 dilution of the cleanser composition in Table demonstrated a 5.70-log reduction (99.9998%) for *Candida albicans* according to the ASTM E2315 test method.

Upon information and belief, the efficacy of the above solutions is further enhanced based upon in-vitro evaluations of oral mucosal cell toxicity studies of surfaces treated with the cleaning and the protective film forming formulations. The studies establish that the formulations do not adversely impact mucosal cell growth or metabolism.

Accordingly, the formulations, process of using the formulations, and articles treated with the formulations offer great benefits with regard to oral care. As such, the invention offers benefits to both full and partial dentures as well as other removable oral appliances such as; retainers, orthodontic braces, removable braces (Invisalign™), athletic mouthguards, anti-snoring devices, TMJ splints, grind prevention devices, whitening trays, infant oral devices (pacifiers, baby bottle nipples, teething rings), reusable hydration devices and beverage straws, or other medical or commercial oral devices, and provides for a surface protection on such oral device surfaces.

Further, the compositions and process taught herein may be used to clean and/or provide a protective coating via applications by a dentist, physician, or orthodontist to oral appliances that are not easily removed including implants and other artificial surfaces that offer functional or cosmetic equivalents of teeth. The compositions could be incorporated into a non-reactive carrier material for applying to more permanent oral appliances and apparatuses. In addition, these permanent or semi-permanent oral devices may be pretreated with a higher concentration of SiQAC coating before attaching or implanting into oral cavity. This pretreatment or extra-strength treatment may range from at about 1% to about 5% of SiQAC.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention. In addition, it should be understood that aspects of the various embodiments may be interchanged, both in whole, or in part. Therefore, the spirit and scope of the invention should not be limited to the description of the preferred versions contained therein.

The invention claimed is:

1. A process of cleaning an oral appliance comprising the steps of:

providing a cleaning composition concentrate comprising, in weight percent, water in an amount of about 49.38%;

citric acid in an amount of about 12.5%;

potassium hydroxide 45 weight % concentration in the amount of about 22.7%;

ethoxylated fatty alcohol surfactant in an amount of about 0.17%;

N-alkyl $C_{12}$-$C_{18}$ dimethyl benzyl ammonium chloride in the amount of about 10.25%;

tetrasodium ethylenediaminetetraacetate in the amount of about 5.0%;

diluting the cleaning composition concentrate with water to a concentration of between about 1:25 to about 1:125, thereby providing a working solution;

exposing a surface of the oral appliance to the working solution;
subsequently exposing the surface of the oral appliance to an anti-microbial coating solution comprising a quaternary ammonium organosilane according to the structure of:

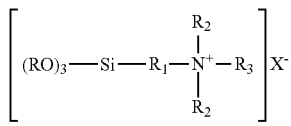

Wherein:
R is an alkyl group, of $C_1$-$C_4$;
$R_1$ is an alkyl group of $C_1$-$C_8$;
$R_2$ is an alkyl group of $C_1$-$C_8$;
$R_3$ is an alkyl group of $C_{11}$-$C_{22}$; and
X is the counter ion of $Cl^-$ or $Br^-$
wherein, the treated oral appliance has a sanitized surface, the sanitized surface has the anti-microbial coating comprising the quaternary ammonium organosilane.

2. A process of providing an antibacterial coating to a surface of an oral appliance comprising the steps of:
supplying a film coating composition concentrate comprising a quaternary ammonium organosilane according to the, structure of:

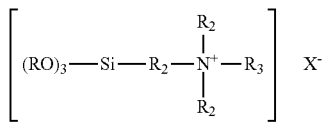

wherein:
R is an alkyl group, of $C_1$-$C_4$;
$R_1$ is an alkyl group of $C_1$-$C_8$;
$R_2$ is an alkyl group of $C_1$-$C_8$;
$R_3$ is an alkyl group of $C_{11}$-$C_{22}$; and
X is the counter ion of $Cl^-$ or $Br^-$;
wherein the film coating composition concentrate comprises in weight percent:
water in an amount of about 48.38%;
citric acid in an amount of about 12.50%;
potassium hydroxide 45 weight % concentration in an amount of about 22.78%;
ethoxylated fatty alcohol surfactant in an amount of about 0.17%;
N—N-alkyl $C_{12}$-$C_{18}$ dimethyl benzyl ammonium chloride in amount of about 10.25%;
tetrasodium ethylenediaminetetraacetate in the amount of about 5%; and
3-(trimethoxysillyl) propyldimethylocatedcyl ammonium chloride;
diluting the film coating composition concentrate with water to about 1:25 to about 1:125; and applying the diluted film coating composition concentrate to the surface of an oral appliance thereby providing an antibacterial coating to the surface of the oral appliance.

3. A process of surface treating an oral appliance comprising the steps of:
providing a cleaning composition concentrate consisting of, in weight percent;
water in an amount of 49.38%;
citric acid in an amount of 12.5%;
potassium hydroxide 45 weight % concentration in the amount of 22.7%;
ethoxylated fatty alcohol surfactant in an amount of 0.17%;
N-alkyldimethyl benzyl ammonium chloride $C_{12}$-$C_{18}$ in the amount of 10.25%;
tetrasodium ethylenediaminetetraacetate in the amount of 5.0%;
diluting the cleaning composition concentrate with water to a concentration of between about 1:25 to about 1:125, thereby providing a working solution;
treating the oral appliance with the working solution;
subsequently exposing the surface of the oral appliance to an anti-microbial coating solution comprising a quaternary ammonium organosilane,
water in an amount of 48.38%;
citric acid in an amount of 12.50%,
potassium hydroxide in an amount of 22.78%;
ethoxylated fatty alcohol surfactant in an amount of 0.17%;
N-alkyl $C_{12}$-$C_{18}$ dimethyl benzyl ammonium chloride in an amount of 10.25%;
tetrasodium ethylenediaminetetraacetate in the amount of about 5.0%; and,
3-(trimethoxysillyl) propyldimethylocatedcyl ammonium chloride;
wherein, the treated oral appliance has a sanitized surface, the sanitized surface has the anti-microbial coating comprising the quaternary ammonium organosilane.

4. The process according to claim 1, wherein the antimicrobial coating solution further comprises a 1:25 to a 1:125 dilution of a concentrated coating solution, wherein the concentrated coating solution comprises in weight percent:
water in an amount of about 48.38%;
citric acid in an amount of about 12.50%;
potassium hydroxide 45 weight % concentration in an amount of about 22.78%;
ethoxylated fatty alcohol surfactant in an amount of about 0.17%;
N-alkyl $C_{12}$-$C_{18}$ dimethyl benzyl ammonium chloride in an amount of about 10.25%;
tetrasodium ethylenediaminetetraacetate in the amount of about 5.0%; and
3-(trimethoxysillyl) propyldimethylocatedcyl ammonium chloride.

* * * * *